United States Patent [19]

Benedict

[11] Patent Number: 4,914,249

[45] Date of Patent: Apr. 3, 1990

[54] DEHYDROGENATION OF DEHYDROGENATABLE HYDROCARBONS

[75] Inventor: Bryan L. Benedict, Evanston, Ill.

[73] Assignee: UOP, Des Plaines, Ill.

[21] Appl. No.: 290,478

[22] Filed: Dec. 29, 1988

[51] Int. Cl.[4] .............................................. C07C 5/32
[52] U.S. Cl. .................................. 585/443; 585/441; 585/444; 585/627; 585/629
[58] Field of Search ............... 585/441, 443, 444, 627, 585/629

[56] References Cited

U.S. PATENT DOCUMENTS

| | | | |
|---|---|---|---|
| 3,380,931 | 4/1968 | Ryland | 252/432 |
| 3,437,703 | 4/1969 | Reitmeier et al. | 260/669 |
| 3,670,044 | 6/1972 | Drehman et al. | 260/683 |
| 3,855,330 | 12/1974 | Mendelsohn et al. | 260/669 |
| 4,113,656 | 9/1978 | Riley et al. | 252/439 |
| 4,376,724 | 3/1983 | Mita et al. | 252/460 |
| 4,418,237 | 11/1983 | Imai | 585/443 |
| 4,435,607 | 3/1984 | Imai | 585/443 |
| 4,565,898 | 1/1986 | O'Hara et al. | 585/444 |
| 4,652,687 | 3/1987 | Imai et al. | 585/319 |
| 4,717,779 | 1/1988 | Bricker et al. | 585/443 |
| 4,717,781 | 1/1988 | Imai et al. | 585/441 |

*Primary Examiner*—Curtis R. Davis
*Attorney, Agent, or Firm*—Thomas K. McBride; Raymond H. Nelson

[57] ABSTRACT

Dehydrogenatable hydrocarbons may be subjected to a dehydrogenation reaction in which the hydrocarbons such as ethylbenzene are contacted with a dehydrogenation catalyst comprising a modified iron compound in the presence of steam. The reaction mixture effluent containing unconverted hydrocarbons, dehydrogenatable hydrocarbon, hydrogen and steam is then contacted with an oxidation catalyst in a second oxidation zone whereby hydrogen is selectively oxidized to the substantial exclusion of oxidation of the hydrocarbon. The selective oxidation catalyst which is employed is prepared in a two-step process in which a compound containing a noble metal of Group VIII of the Periodic Table and a compound containing a metal of Group IVA of the Periodic Table is impregnated on a porous inorganic support such as alumina. The impregnated support is then calcined and subjected to a second step impregnation in which the support is impregnated with a solution of a compound containing lithium. Following this the support is then dried and calcined.

17 Claims, No Drawings

DEHYDROGENATION OF DEHYDROGENATABLE HYDROCARBONS

BACKGROUND OF THE INVENTION

It has been known in the prior art that unsaturated hydrocarbons may be obtained from the dehydrogenation of dehydrogenatable hydrocarbons. The dehydrogenation may be effected by subjecting the dehydrogenatable hydrocarbons to a dehydrogenation process at dehydrogenation conditions in the presence of certain catalytic compositions of matter which possess the ability to dehydrogenate said compounds with the resultant formation of olefinic hydrocarbons. The particular dehydrogenation catalysts which are employed are well known in the art and comprise such compounds as nickel composited on a solid support such as diatomaceous earth, kieselguhr, charcoal and iron composited on the same supports, etc.

Other dehydrogenation processes have employed, in addition to the dehydrogenation catalysts, an oxidation catalyst in the reaction process. The presence of the oxidation catalyst is necessitated by the fact that it is advantageous to oxidize the hydrogen which is produced by contact with an oxygen-containing gas in order to maintain the desired reaction temperature. For example, styrene, which is an important chemical compound utilized for the preparation of polystyrene, plastics, resins or synthetic elastomers such as styrene-butadiene rubber, etc., may be prepared from the dehydrogenation of ethylbenzene. The dehydrogenation of ethylbenzene into styrene, which is effected by treating ethylbenzene with steam in the presence of a modified iron catalyst, is endothermic in nature. The heat of reaction is about 30 Kcal per mole of ethylbenzene. Therefore, the temperature of the catalyst bed decreases significantly during the progress of the reaction in a commercial adiabatic reactor resulting in limitation of ethylbenzene conversion to a low level. The limitation of conversion arises from the fact that the equilibrium conversion of ethylbenzene is lowered and the rate of ethylbenzene dehydrogenation decreases as the reaction temperature decreases. The decrease of temperature adversely affects not only the conversion level, but also the selectivity for styrene, since at equilibrium conditions, only undesirable side reactions continue to take place. Therefore, it is necessary to maintain the desired temperature level in order to provide a high equilibrium conversion level and a high reaction rate. In the conventional process, the maintenance of temperature is attained by reheating the product stream with the addition of superheated steam between dehydrogenation catalyst beds using a multicatalyst bed reactor system. However, consumption of the additional superheated steam is considerably high and makes the dehydrogenation process costly. Accordingly, significant process economic improvements over the conventional ethylbenzene dehydrogenation processes can be achieved if the reaction temperature is somehow maintained while eliminating or reducing the additional superheated stream. One method of providing for the maintenance of the reaction temperature is to introduce oxygen into the reaction mixture by way of oxygen or an oxygen-containing gas such as air which will burn the hydrogen formed during the dehydrogenation reaction, this combustion resulting in an exothermic reaction which will provide the necessary amount of heat and, in addition, will shift the equilibrium toward production of styrene since the hydrogen formed in the dehydrogenation is consumed. Consequently, a higher conversion and high styrene selectivity are achievable.

The combustion of hydrogen with the oxygen in the oxygen-containing gas requires the presence of an oxidation catalyst. There are some key requirements for the oxidation catalyst to be usable for such a purpose. The most important catalytic property required is good catalytic stability since the oxidation catalyst must survive under very severe reaction conditions, namely at about 600° C. to 650° C. in the presence of steam. Under such conditions, porous inorganic materials such as α-aluminas, silicas and zeolites cannot maintain their pore structures for a long period of time, resulting in the permanent damage of catalysts prepared using such materials as supports, e.g., platinum supported on a porous high surface area alumina, silica, or zeolite. Secondly, the oxidation catalyst must be very active to achieve complete conversion of oxygen to avoid poisoning of iron-based dehydrogenation catalysts which are sensitively oxidized with oxygen to lose their dehydrogenation activities. Thirdly, the oxidation catalyst must be selective for oxidation of hydrogen. Otherwise, ethylbenzene and styrene are consumed to lower the efficiency of styrene production.

Various U.S. patents have described types of oxidation catalysts which may be employed in this process. For example, U.S. Pat. No. 3,437,703 describes a catalytic dehydrogenation process which employs, as a dehydrogenation catalyst, a composition known in the trade as Shell-105 which consists of from 87% to 90% ferric oxide, 2% to 3% chromium oxide, and from 8% to 10% of potassium oxide. In addition, another dehydrogenation catalyst which is employed comprises a mixture of nickel, calcium, chromic oxide, graphite with a major portion of a phosphate species. In addition to these dehydrogenation catalysts, the reaction also employs a catalyst for the oxidation step of the process comprising platinum or palladium in elemental from or as a soluble salt. Another U.S. patent, namely 3,380,931, also discloses an oxidation catalyst which may be used in the oxidative dehydrogenation of compounds such as ethylbenzene to form styrene comprising an oxide of bismuth and an oxide of a metal of Group VIB of the Periodic Table such as molybdenum oxide, tungsten oxide or chromium oxide. In addition, the patent also states that minor amounts of arsenic may also be present in the catalytic composite as well as other metals or metalloids such as lead, silver, tin, manganese, phosphorus, silicon, boron and sulfur.

U.S. Pat. No. 3,855,330 discloses a method for the production of styrene in which ethylbenzene is treated in the vapor state by passage over a dehydrogenation catalyst and an oxidation catalyst while introducing oxygen into the reaction medium. The dehydrogenation catalysts which are employed are those which have been set forth in various prior U.S. patents and which may be similar in nature to the dehydrogenation catalysts previously discussed. The types of oxidation catalysts which may be employed will include platinum or palladium catalysts which are composited on alumina or molecular sieves zeolite-type which have been charged with ferrous, heavy or noble metals. The patent lists the types of catalysts which are employed including copper or various zeolites, platinum on alumina, platinum on spinel, platinum and sodium on zeolites, platinum, sodium and potassium on zeolites, etc.

U.S. Pat. No. 3,670,044 discloses a method for dehydrogenating cycloalkane, arylalkane and alkanes in the presence of gaseous hydrogen or mixture of gaseous hydrogen and gaseous oxygen using a catalyst composition comprising a Group VIII metal or a mixture of a Group VIII metal and a Group IVA metal deposited on a support comprising a Group II aluminate spinel. It is noted that the patentee teaches that added hydrogen is used in connection with the oxygen, and that when only oxygen is used, the conversion and selectivity are generally low. The addition of hydrogen is believed to be a significant disadvantage in the dehydrogenation process inasmuch as the equilibrium conversion is lowered. This is in contradistinction to the process of the present invention wherein the dehydrogenation process, prior to the oxidation step, is not effected in the presence of any added hydrogen. As will hereinafter be shown in greater detail, the present process results in the selective oxidation of hydrogen with a concomitantly lower selectivity to carbon monoxide and carbon dioxide. In addition, the patentee teaches the use of one catalyst for both dehydrogenation and oxidation which is in contrast to the separate dehydrogenation and oxidation catalysts which are used in the present process.

Other U.S. patents which pertain to catalytic compositions of matter include U.S. Pat. No. 4,113,656 which describes a process for achieving the distribution of metals on a support which requires quite small particles of the carrier as a nucleating agent for the catalytic metal deposited thereon. In addition, U.S. Pat. No. 4,376,724 discloses the dispersion of rhodium on a silica or titania support in which the metal is dispersed on the support in what is referred to as an eggshell distribution.

In addition to the aforementioned United States patents other patents disclose a method for the dehydrogenation of dehydrogenatable hydrocarbons utilizing a two-step process which includes dehydrogenation followed by a selective oxidation process. U.S. Pat. No. 4,435,607 discloses an oxidation catalyst which may, if so desired, contain a metal of Group IA or IIA of the Periodic Table, the present species of these metals including potassium, rubidium, cesium, barium, francium, radium, these metals if present in the catalyst composite being impregnated on the solid support containing a Group VIII metal and Group IVA metal in a third impregnation. U.S. Pat. No. 4,418,237 also discloses an oxidative catalyst comprising a noble metal of Group VIII of the Periodic Table and a metal cation which possesses an ionic radius no less than 1.35 Angstroms, and particularly those in Group IA and IiA which fall within this definition. U.S. Pat. No. 4,652,687 discloses an oxidation catalyst comprising a Group VIII noble metal, a Group IVA metal and a Group IA or IiA metal composited on a metal oxide support which possesses a particular configuration. Again the impregnation of the metals on the support may be effected in a coimpregnation method or stepwise. U.S. Pat. No. 4,717,779 also discloses a process for the dehydrogenation of dehydrogenatable hydrocarbons utilizing a noble metal of Group VIII and a metal of Group IVA composited on a solid inorganic support and, if so desired, may also contain a metal selected from Groups IA and IIA of the Periodic Table.

As will hereinafter be shown in greater detail it has now been discovered that by preparing a selective oxidation catalyst by coimpregnating a Group VIII noble metal and a Group IVa metal on a solid porous support followed by a sequential impregnation of lithium on the previously impregnated and calcined support it is possible to obtain a superior catalyst with relation to stability and performance as measured by activity and selectivity than the properties which are possessed by catalysts which have been used in prior processes.

BRIEF SUMMARY OF THE INVENTION

This invention relates to a process for the dehydrogenation of dehydrogenatable hydrocarbons. More specifically, the invention is concerned with a process for the dehydrogenation of a dehydrogenatable hydrocarbon in which the hydrocarbon which is to undergo treatment is subjected to a dehydrogenation step in the presence of a dehydrogenation catalyst. This dehydrogenation step is followed by a selective oxidation step in which the product mixture which results from the aforementioned dehydrogenation step is treated in the presence of certain catalytic compositions of matter which are hereinafter set forth in greater detail in such a manner whereby the hydrogen which is present and which has resulted from the dehydrogenation step is selectively oxidized with a concomitant minimum oxidation of the hydrocarbons. By utilizing the particular selective oxidation catalyst, it is possible to obtain the desired dehydrogenated hydrocarbons in a relatively high yield as well as maintaining the stability and activity of the catalyst to a greater degree than has heretofore been experienced. By maintaining the aforementioned stability and activity, it is possible to obviate the necessity for relatively frequent changes of the catalyst or, in the alternative, regenerating the catalyst, thereby adding to the commercial attractiveness and economical feasibility of the dehydrogenation process.

It is therefore an object of this invention to provide a process for the dehydrogenation of dehydrogenatable hydrocarbons.

A further object of this invention is to provide a catalyst for the selective oxidation step of the process whereby hydrogen which is formed during the dehydrogenation process will be selectively oxidized to the substantial exclusion of the oxidation of the hydrocarbons.

In one aspect an embodiment of this invention resides in a process for the dehydrogenation of a dehydrogenatable hydrocarbon with separate and intermediate selective oxidation of hydrogen which comprises the steps of:

(a) contacting said hydrocarbon with a dehydrogenation catalyst comprising an alkaline metal-promoted iron compound in a first reaction dehydrogenation zone in the presence of steam at dehydrogenation conditions to produce a first reaction dehydrogenation zone effluent stream comprising a mixture of dehydrogenated hydrocarbons, unconverted hydrocarbons, hydrogen and steam;

(b) removing said first reaction dehydrogenation zone effluent stream from said first dehydrogenation zone;

(c) passing said effluent stream of step (b) to a second reaction oxidation zone which is separate and discrete from said first reaction dehydrogenation zone;

(d) contacting said first dehydrogenation zone effluent stream in said second reaction oxidation zone with oxygen-containing gas in the presence of an oxidation catalyst consisting essentially of a Group VIII noble metal, a Group IVA metal, and lithium composited on a solid porous support at oxidation conditions to selectively oxidize said hydrogen within said first reaction zone effluent stream to the substantial exclusion of oxidation of said dehydrogenated and unconverted hydrocarbons, wherein said selective oxidation of said hydrogen is exothermic in nature to provide additional heat and thereby raise the temperature of said dehydrogenated and unconverted hydrocarbons;

(e) withdrawing a dehydrogenated and unconverted hydrocarbon effluent stream from said second reaction oxidation zone having an increased temperature with respect to the temperature of said first reaction dehydrogenation zone effluent stream;

(f) passing said second reaction oxidation zone product effluent stream of step (e) at dehydrogenation conditions to a third reaction dehydrogenation zone containing a dehydrogenation catalyst comprising an alkaline metal-promoted iron compound to produce dehydrogenated hydrocarbons; and (g) withdrawing and recovering said dehydrogenated hydrocarbons, the improvement which comprises utilizing as said selective oxidation catalyst a composite which has been prepared by the steps of impregnating a solid porous support with a compound containing a Group VIII noble metal and a compound containing a Group IVA metal, calcining said impregnated support and sequentially impregnating said calcined impregnated support with a compound containing lithium.

A specific embodiment of this invention is found in a process for the dehydrogenation of ethylbenzene which comprises contacting said ethylbenzene with a hydrogenation catalyst comprising an alkaline metal modified iron catalyst with a temperature in the range of from about 500° C. to about 700° C. and a pressure in the range of from about 0.1 to about 10 atmospheres in the presence of steam, thereafter contacting the resultant mixture of unconverted ethylbenzene, styrene, hydrogen and steam with air at a temperature in the range of from about 500° to about 700° C. and a pressure in the range of from about 0.1 to about 10 atmospheres in the presence of a catalyst which has been prepared by impregnating an alumina support with a platinum containing compound and a tin containing compound, calcining the resultant impregnated support, and thereafter impregnating and recalcining the previously calcined support with a lithium containing compound, and recovering the desired styrene after the final stage of dehydrogenation.

Other objects and embodiments will be found in the following detailed description of the invention.

DETAILED DESCRIPTION OF THE INVENTION

As hereinafter set forth the present invention is concerned with a dehydrogenation process for the dehydrogenation of dehydrogenatable hydrocarbons which involves the use, in one step of the process, of a selective oxidation catalyst which will provide an improved stability and selectivity as well as increasing the activity, as exemplified by the conversion of oxygen as well as eliminating some disadvantages which have been present when utilizing prior catalytic compositions of matter in the same process.

In the present process, a dehydrogenatable hydrogen of the type hereinafter set forth in greater details is contacted with a dehydrogenation catalyst in the presence of steam in a multicatalyst bed system. Inasmuch as the dehydrogenation of the hydrocarbon is endothermic in nature, it is necessary to provide an additional amount of heat before the product enters the next catalyst bed in order to provide a high equilibrium conversion as well as a high reaction rate. One method of effecting this increase in the desired temperature is to provide an internal catalytic combustion of the hydrogen which is produced during the dehydrogenation reaction in order to reheat the product to the desired level. By effecting a selective oxidation of the hydrogen, it is possible to avoid the use of superheated steam or other outside sources of heat. This selective oxidation of hydrogen with the resultant composition thereof is effected by utilizing a selective oxidation catalyst of the type hereinafter set forth in greater detail, the selective oxidation catalyst maintaining its stability and activity for a considerable length of time.

The process of the present invention may be effected by utilizing an apparatus in which the dehydrogenation catalyst and the oxidation catalyst, both of the type hereinafter set forth in greater detail, are loaded in the apparatus in alternate layers. The number of alternate layers of dehydrogenation catalyst and selective oxidation catalyst may vary according to the size or type of apparatus which is employed, the number of alternate layers ranging from three to about nine. As will hereinafter be shown, the dehydrogenation catalyst and the oxidation catalyst are different in nature. Examples of dehydrogenation catalysts which may be employed will comprise an alkaline earth metal-promoted iron compound. The term "alkaline metal" as used in the present specification and appended claims will refer to metals of Groups IA and IIA of the Periodic Table which include lithium, sodium, potassium, rubidium, cesium, beryllium, magnesium, calcium, strontium and barium. In addition, the promoted iron compound catalyst will, in the preferred embodiment of the invention, also include a compound containing a metal of Groups IVB, VB and VIB of the Periodic Table. For example, a typical dehydrogenation catalyst which may be employed in the process of this invention will consist essentially of about 85% by weight of ferric oxide, 12% by weight of potassium hydroxide, 2% by weight of chromia and 1% by weight of sodium hydroxide. Another typical dehydrogenation catalyst which may be used comprises 90% by weight of ferric oxide, 4% by weight of chromia and 6% by weight of potassium carbonate. In addition these catalysts, other well-known dehydrogenation catalysts which may be utilized will include those comprising ferric oxide, potassium oxide, as well as other metal oxides and/or sulfides of metals of Groups IA, IIA, IVB, VB and VIB of the Periodic Table including those of calcium, lithium, strontium, magnesium, beryllium, zirconium, tungsten, molybdenum, hafnium, vanadium, copper, chromium and mixtures of two or more oxides such as chromia-alumina, chromia-titania, alumina-vanadia and the like.

The dehydrogenation of a dehydrogenatable hydrocarbon such as, for example, ethylbenzene, is effected by contacting the dehydrogenatable hydrocarbon and steam, in the absence of any added hydrogen, with the aforesaid catalyst at dehydrogenation conditions which are in the range of from about 500° to about 700° C. and at a reaction pressure in the range of from about 0.1 to about 10 atmospheres; the exact dehydrogenation conditions are, however, a function of the particular dehydrogenatable hydrocarbon undergoing dehydrogenation. Other reaction conditions will include a Liquid Hourly Space Velocity based on the hydrocarbon charge of from about 0.1 to about 10 hrs$^{-1}$ and steam to hydrocarbon weight ratios ranging from about 1:1 to about 40:1. The number of dehydrogenation zones of the catalyst beds may vary from 1 to about 5 in number and typically may comprise three reaction zones; however, the number of zones is not critical to the invention. After contacting the dehydrogenation catalyst with the steam and hydrocarbon, the resulting mixture comprising unconverted hydrocarbon, dehydrogenated hydrocarbon, steam and hydrogen which has passed through the catalyst bed is contacted in a separate zone with the selective oxidative catalytic composition of the type hereinafter set forth in greater detail. In addition, oxygen-containing gas is introduced into the reactor, preferably at a point adjacent to the oxidation catalyst bed. Examples of oxygen-containing gases which may be utilized to effect the selective oxidation of the hydrogen which is present will include air, oxygen, air or oxygen diluted with other gases such as steam, carbon dioxide and inert gases such as nitrogen, argon, helium, etc. The amount of oxygen which is introduced to contact the product stream may range from about 0.1:1 to about 2:1 moles of oxygen per mole of hydrogen contained in the product stream. In this particular reaction zone, the product stream, which comprises unreacted dehydrogenatable hydrocarbon, dehydrogenated hydrocarbon, hydrogen and steam, undergoes a selective oxidation in contact with oxygen and the oxidation catalyst whereby hydrogen is selectively oxidized to water with a minimal amount of reaction of oxygen with the hydrocarbons, either unconverted hydrocarbon or dehydrogenated hydrocarbon. The selective oxidation of hydrogen is important inasmuch as the competing reaction to this oxidation reaction comprises the oxidation of the unconverted hydrocarbons such as ethylbenzene or the dehydrogenated hydrocarbon such as styrene. The combustion of the hydrocarbons with oxygen has a two-fold deleterious effect on the overall reaction in that (1) the combustion of the hydrocarbons leads to the loss of product and (2) the combustion reaction leads to the production of carbon monoxide. The production of carbon monoxide in the effluent stream from the oxidation zone to a subsequent dehydrogenation zone will detrimentally affect the performance of the dehydrogenation catalyst in the second dehydrogenation zone, thus further lowering the yield of the desired dehydrogenated hydrocarbon.

After passage through the zone containing the oxidation catalyst, the mixture may then be passed through a second dehydrogenation zone containing a dehydrogenation catalyst of the type hereinbefore set forth for further dehydrogenation, the process being completed through the plurality of zones followed by withdrawal of the product stream and separation of the unconverted hydrocarbon from the desired dehydrogenated product.

It is contemplated that the dehydrogenation process for the dehydrogenation of dehydrogenatable hydrocarbons utilizing the oxidative catalytic compositions of matter of the present invention will be applicable to a wide variety of dehydrogenatable hydrocarbons. Examples of hydrocarbons which are susceptible to a dehydrogenation process utilizing the catalysts of the present invention will include lower alkyl-substituted aromatic hydrocarbons such as ethylbenzene, diethylbenzene, isopropylbenzene, diisopropylbenzene, o-ethyltoluene, m-ethyltoluene, p-ethyltoluene, o-isopropyltoluene, m-isopropyltoluene, p-isopropyltoluene, ethylnaphthalene, propylnaphthalene, isopropylnaphthalene, diethylnaphthalene, etc., paraffins such as ethane, propane, n-butane, isobutane, n-pentane, isopentane, n-hexane, n-heptane, n-octane, n-nonane, n-decane, and branched chain isomers thereof, cycloparaffins such as cyclobutane, cyclopentane, cyclohexane, methylcyclopentane, methylcyclohexane, ethylcyclopentane, olefins such as ethylene, propylene, 1-butene, 2-butene, 1-pentene, 2-pentene, 1-hexene, 2-hexene, 2-hexene, 3-hexene, and branched chain derivatives thereof, etc.

The selective oxidation step of the process utilizes, as hereinbefore set forth, the hydrogen which has been produced in the dehydrogenation step of the process to supply heat to the inlet of the next dehydrogenation catalyst bed. Inasmuch as temperatures which are utilized in the process may be as high as 650° C. in the presence of steam, the operating conditions in which the oxidation catalyst must function are severe in nature. In order for the oxidation catalyst to remain stable and minimize the carbon formation thereon, the catalyst support must be calcined at a relatively high temperature in order to decrease the surface area, this descrease in surface area contributing to the stability of the catalyst. Conventional oxidation catalysts utilizing a porous support such as alumina which had been calcined at relatively low temperatures, i.e., below about 900° C. or lower, lose surface area at a rapid and form excessive carbon on the surface thereof, thus resulting in a deactivation of the catalyst.

The particularly effective oxidation catalyst which may be used in the dehydrogenation and subsequent selective process of the present invention comprises a noble metal of Group VII of the Periodic Table as exemplified by platinum along with a Group IVA metal of the Periodic Table such as tin plus lithium composited on a solid porous inorganic oxide support. This type of inorganic oxide support is not critical to this invention, however, a particularly effective support which contributes to the stability and effectiveness of the catalyst comprises an alumina. The alumina support will be derived from various types of aluminas such as, for example, boehmite, pseudoboehmite, gibbsite, etc., or a precursor of an alumina such as an aluminum hydroxyl chloride sol. The calcination of the support is effected at a temperature within the range of from about 600° to about 1500° C. prior to impregnation of the metals thereon. If so desired, the calcination of this support may be effected in a dry atmosphere, preferably at a temperature in the range of from about 800° to about 1500° C. or the calcination may be effected in a hydrous atmosphere such as that provided by steam, the temperatures preferably in the range of from about 600° to about 1300° C. The calcination of the support within these temperature ranges will be effected over a period of time which may range from about 0.5 to about 30 hours or more in duration and it is to be understood that the particular temperature which is selected for the calcination of the support will influence or direct the time frame during which the calcination takes place. It has been found that a particularly effective type of alumina source which may be in the form of pellets, spheres, powder, slurry, etc. and which will provide desired catalyst support. In addition, the alumina may be present as alpha-alumina or as a mixture of alpha-alumina and theta-alumina.

As was hereinbefore set forth, the selective oxidation catalysts which are employed in the process of this invention will comprise a noble metal of Group VIII of the Periodic Table and a metal of Group IVA of the Periodic Table composited on a solid inorganic support which, prior to the compositing of the metals thereon, has been calcined at a temperature within the range herebefore discussed. In addition, if so desired, it is also contemplated within the scope of this invention that the catalyst will also contain a metal selected from Groups IA and IIA of the Periodic Table. Of the noble metals of Group VIII of the Periodic Table, platinum, palladium and rhodium comprise the preferred species, said metals being present in the final composite in an amount in the range of from about 0.01% to about 5% by weight. Of the metals of Group IVA of the Periodic Table, germanium, tin and lead comprise the preferred species, these metals also being present in the final catalyst composite in an amount in the range of from about 0.005% to about 5% by weight.

The catalytic metal portions of the finished catalyst comprising the Group VIII noble metal and Group IVA metal are impregnated on the surface of the catalyst support in a coimpregnation process. For example, in one method of preparation the Group VIII noble metal and Group IVA metal may be coimpregnated through the formation of a complex in the impregnation solution. The formation of this complex constitutes a significant factor inasmuch as the complex formed between the two metals is bulky in nature and its adsorption properties are such that it is deposited on the exterior surface of the catalyst particle during the impregnation step thereby insuring the deposition of a higher average concentration of Group VIII metal in the aforesaid exterior surface. In one embodiment of the invention the formation of the complex is accomplished by utilizing tin of the type hereinbefore set forth in greater detail in a +2 form. Alternatively, if tin is in a +4 form or other Group IVA metals are used a complex may be effected by utilizing, in the impregnation solution, a compound which possesses both a functional group as exemplified by a thio, amino, hydroxyl, or phosphorus moiety as well as a polar group such as a carboxyl or hydroxyl moiety in the compound. Examples of these compounds will include thiomalic acid, thiolactic acid, ethylenediaminetetraacetic acid, thioglycolic acid, thiopropionic acid, thiodiacetic acid, thiodipropionic acid, etc. It is to be understood that these compounds are only representative of the type of complexing compounds which may be employed, and that the present invention is not necessarily limited thereto.

Another alternative method of preparing the desired selective oxidation catalyst of the present invention is to impregnate the alumina support with a Group IVA metal which may be in the form of beads, spheres, pellets, etc. with an aqueous solution of the metal of Group IVA of the Periodic Table in which a soluble salt such as tin chloride, tin bromide, tin sulfate, lead chloride, lead persulfate, germanium chloride, etc. is present in the solution in an amount sufficient so that the finished catalytic composite will contain the desired amount of the metal. The impregnation is allowed to proceed for a predetermined period of time following which the composite is recovered, dried and calcined. Alternatively, the group IVA metal may be incorporated into the alumina during the alumina forming step, by employing a suitable Group IVA containing compound. In this case, the Group IVA compound may be added to an alumina sol or alumina dough which may be oil-dropped or extruded to form the desired alumina composite. The composite is dried and calcined to form the final support containing Group IVA metal. Thereafter the Group IVA metal containing alumina support is then surface-impregnated with an aqueous solution of a noble metal of Group VIII of the Periodic Table and, if so desired, a polar compound which assists in the surface-impregnation of the Group VIII noble metal in an amount sufficient to provide the desired amount of the metals in the finished catalytic composite. For example, it is possible to employ a soluble salt of a noble metal of Group VIII of the Periodic Table such as chloroplatinic acid, chloropalladic acid, rhodium chloride, platinum sulfate, palladium sulfate, etc. After allowing the impregnation to proceed for a period of time sufficient to permit the deposition of the desired amount of metal on the catalyst support, the composite is recovered, dried and calcined at a temperature in the range of from about 500° to about 600° C. or more in an air or air-steam atmosphere and recovered.

The second step of the preparation of the catalyst of the present invention will comprise impregnation the solid support containing the Group VIII noble metal and Group IVA metal with a lithium containing compound. As will hereinafter be shown in greater detail the two-step process for preparing the selective oxidation catalyst according to the process of this invention will result in the obtention of a catalyst which possesses greater activity and stability than will be found in those catalysts which contain no lithium or which have been prepared by a coimpregnation of Group VIII noble metal, group IVA metal and lithium. The catalytic activity of the selective oxidation catalyst is obtained by the presence of catalyst on the alumina support which serves as the active oxidation site. The presence of a Group IVA metal such as tin is necessary in order to attenuate the active oxidation sites due to the electron withdrawing nature of the Group IVA metal. By incorporating lithium in a second impregnation step on the catalyst it has been found that the lithium neutralizes or passivates the acidic sites on the alumina which could lead to undesirable hydrocarbon side reactions such as coking. The presence or formation of coke on the surface of the catalyst is undesirable inasmuch as it will lead to a loss of activity and thus necessitate replacement of the catalyst at shorter intervals, thus contributing to the possibility of rendering the process uneconomical to operate.

The impregnation of the Group VIII noble metal and Group IVA metal containing porous support may be effected in a suitable manner similar in nature to the first impregnation step, that is, by utilizing an aqueous solution of a soluble lithium containing compound such as lithium chloride, lithium nitrate, lithium acetate, lithium bicarbonate, lithium borate, lithium dithionate, lithium fluorosulfonate, lithium iodide, lithium perchlorate, etc. The porous support is impregnated with a solution containing the lithium containing compound in an amount sufficient to provide a finished catalyst composite which will contain from about 0.05% to about 5% by weight of the catalyst composite. After effecting the impregnation with the lithium containing compound the catalyst composite is recovered, dried and calcined at a temperature of from about 500° to about 650° C. in an air or air-steam atmosphere in a manner similar to that hereinbefore set forth and recovered.

Some specific examples of selective oxidation catalytic compositions of matter which may be used in the dehydrogenation process and which have been prepared according to the process previously described in which the noble metals of Group VIII and metals of Group IVA have been impregnated on an alumina support, calcined and subsequently impregnated in a second step with lithium followed by calcination will include platinum, germanium and lithium composited on alumina, palladium, germanium and lithium composited on alumina, rhodium, germanium and lithium composited on alumina, platinum, tin and lithium composited on alumina, palladium, tin and lithium composited on alumina, rhodium, tin and lithium composited on alumina, etc. It is to be understood that the above-enumerated catalysts are only representative of the selective oxidation composites which may be used in the process of this invention, and that said invention is not necessarily limited thereto. By utilizing a selective oxidative catalytic composition of matter in a process which involves the dehydrogenation of dehydrogenatable hydrocarbons, it is possible to obtain a process which, in addition to obtaining a desirable and commercially attractive yield of dehydrogenation products, also permits the operation of the process in an economically viable manner due to the catalytic stability of the catalyst under the relatively harsh and stringent operating conditions such as high temperature and high concentration of steam at which the process is operated.

By utilizing the catalyst which has been prepared by surface impregnating the catalytic metals, it is possible to obtain a catalyst system which exhibits the desired characteristics of stability and activity which is in contradistinction to oxidation catalysts which have been set forth in the prior art, the latter being unable to produce the desired stability which is exhibited by the catalyst of the present invention, and therefore cannot survive in use for a relatively long period of time. This relatively short life of a catalyst discourages the commercial use of such catalysts as unattractive due to the necessity of having to replace or regenerate the catalyst after a short interval of operating time has elapsed. In addition, the catalysts of the present invention also exhibit a definite activity for the selective oxidation of hydrogen rather than a tendency for the oxidation of the dehydrogenated products or unreacted hydrocarbons.

The catalyst of the present invention will exhibit an excellent stability in that it possesses the ability to maintain the maximum temperature of the reaction at a position which is near the inlet of the catalyst bed. The desired reaction, that is, the selective oxidation of hydrogen, is highly exothermic in nature and it is therefore an indication of a good catalyst that the maximum temperature is maintained near the inlet of the catalyst bed, thus indicating that the conversion of the hydrogen occurs at a time shortly after the product stream comprising unconverted hydrocarbons, dehydrogenated hydrocarbons, steam and hydrogen enters the catalyst bed. In addition, as will hereinafter be demonstrated, the catalyst of the present invention also possesses the ability to effect a relatively high conversion of oxygen as is evidenced by the absence of oxygen in the exit gas which is withdrawn from the reaction zone containing the selective oxidation catalyst.

The following examples are given for purposes of illustrating the selective oxidation catalyst of the present invention as well as to a process utilizing the selective oxidation catalyst in said process. However, it is to be understood that these examples are merely illustrative in nature and that the present process is not necessarily limited thereto.

EXAMPLE I

A selective oxidation catalyst was prepared according to the methods heretofore known in the art by impregnating an alumina extrudate which had been previously calcined at a temperature of about 1330° C. with a mixture of a chloroplatinic acid solution, a lithium nitrate solution and a stannous chloride solution, the strength of the solution being sufficient to afford a 0.4 weight percent platinum, a 0.2 weight percent lithium and a 0.35 weight percent tin based on the calcined support. Following this, deionized water was added along with 3% hydrochloric acid to afford an impregnated solution/calcined support base ratio of 0.55/1 (volume/volume). The extrudate base and impregnating solution were charged to a glass jacketed rotary evaporator which was then nitrogen purged and the rotary evaporator was cold rolled for a period of 30 minutes. Following this, steam was charged to the evaporator jacket and the evaporator was hot rolled for a period of 6 hours until the presence of moisture was not detected at the mouth of the evaporator. The impregnated extrudate was then dried and loaded into a quartz tube where it was calcined in a stream of air at a temperature of 520° C. for a period of 1 hour. At the end of this time the catalyst was cooled to ambient temperature in a flowing air stream and recovered. This catalyst was designated as catalyst A.

EXAMPLE II

A second catalyst was prepared according to the known method by coimpregnating an alumina extrudate utilizing chloroplatinic acid, lithium chloride and stannous chloride in an amount sufficient to afford 0.4 weight percent platinum, 0.2 weight percent lithium, and 0.35 weight percent tin based upon the weight of the calcined support. The impregnated support was treated in a method identical to that set forth in Example I above by cold rolling in a glass jacketed rotary evaporator for a period of 30 minutes, thereafter hot rolling the evaporator using steam to afford the heat, followed by calcination at a temperature of 520° C. for a period of 1 hour. This catalyst was labeled catalyst B.

EXAMPLE III

A third selective oxidation catalyst was prepared in a manner similar to that hereinbefore set forth by coimpregnating an alumina extrudate with a chloroplatinic acid solution and a stannous chloride solution in an amount sufficient to afford 0.4 weight percent platinum and 0.35 weight percent tin based on the weight of the calcined support. The difference between this catalyst which was obtained after cold rolling, hot rolling and calcination was that the catalyst composite did not contain any lithium. This catalyst was designated as C.

EXAMPLE IV

The selective oxidation catalyst composite of the present invention was prepared by impregnating an alumina extrudate with a chloroplatinic acid solution and a tin chloride solution in an amount sufficient to afford 0.4 weight percent platinum and 0.35 weight percent tin based on the calcined support. The impregnated solution and the calcined support extrudates were placed in a glass jacketed rotary evaporator which was cold rolled in the presence of nitrogen for a period of 30 minutes. Thereafter steam was charged to the evaporator jacket and the evaporator was hot rolled for a period of 6 hours until the presence of moisture was not detected at the mouth of the evaporator. The impregnated extrudate was then dried and calcined in a stream of air at a temperature of 520° C. for a period of 1 hour. At the end of this time the catalyst was cooled to ambient temperature and recovered.

Following this the impregnated support was then impregnated in a subsequent second impregnation step with a solution of lithium nitrate in an amount sufficient to afford 0.2 weight percent lithium based upon the impregnated support, the amount of lithium nitrate solution being sufficient to afford an impregnated solution/impregnated alumina support ratio of 1/1 (volume/volume). The catalyst base and solution were then placed in the glass jacketed rotary evaporator purged with nitrogen and cold rolled for a period of 15 minutes. Thereafter steam was charged to the evaporator jacket and the evaporator was hot rolled for a period of 2 hours until no moisture was detected at the mouth of the evaporator. The doubly impregnated extrudate was then dried and calcined in a quartz tube in a stream of air for a period of 2 hours while maintaining the temperature at 650° C. At the end of this date the catalyst was cooled to ambient temperature in a flowing air atmosphere. This catalyst was designated as catalyst D.

EXAMPLE V

The catalysts which were prepared according to the above example were then utilized in a selective oxidation process. The catalysts in an amount of 14 cc were loaded into ½" inner diameter stainless steel reactors having a 10" long ½" diameter bore for the catalyst loading. The reactors were heated to an inlet temperature such that the maximum bed temperature was maintained at 600° C. and a feedstock comprising a mixture of 7.3 mole percent nitrogen, 3.9 mole percent hydrogen, 0.8 mole percent oxygen, 8.7 mole percent of a mixture of 36% ethylbenzene and 64% styrene plus 79.2 mole percent of steam was fed to the reactors. The feedstream was passed over the oxidation catalyst beds at the aforesaid inlet temperature at a reactor outlet pressure of 0.7 atmospheres. The feed was maintained at a liquid hourly space velocity of 37 hour$^{-1}$ for a period of 24 hours.

As an indication of the stability and activity of the catalyst, measurements were taken periodically to determine the oxygen conversion and styrene combustion selectivity of the catalyst. The results of these tests are set forth in Tables 1 and 2 below.

TABLE 1

| Oxygen Conversion of Fresh Catalysts (%) | | | | |
|---|---|---|---|---|
| | CATALYST | | | |
| Hours on Stream | A | B | C | D |
| 3 | 98.0 | 97.1 | 93.5 | 98.4 |
| 12 | 96.8 | 94.7 | 87.6 | 98.4 |
| 18 | 96.3 | 94.8 | 85.5 | 97.5 |
| 24 | 96.2 | 94.4 | 82.7 | 97.5 |

TABLE 2

| Styrene Combustion Selectivity of Fresh Catalysts (%) | | | | |
|---|---|---|---|---|
| | CATALYST | | | |
| Hours on Stream | A | B | C | D |
| 3 | 7.5 | 19.5 | 11 | 6.3 |
| 12 | 6 | 11.8 | 7.8 | 5 |
| 18 | 6 | 11 | 7.8 | 5 |

TABLE 2-continued

| Styrene Combustion Selectivity of Fresh Catalysts (%) | | | | |
|---|---|---|---|---|
| | CATALYST | | | |
| Hours on Stream | A | B | C | D |
| 24 | 6 | 10.8 | 7.9 | 5 |

EXAMPLE VI

In order to further differentiate the superior performance of a catalyst prepared according to the process of this invention the catalysts were subjected to a hydrothermal ageing process in order to determine a simulated aged activity. The catalysts were subjected to 24 hours of ageing at a temperature of 800° C. and a pressure at 1 atmosphere to accelerate the platinum agglomeration of the catalyst, said ageing being in the presence of an atmosphere of air and steam.

The ageing process simulated a period of about 1 year of use in a commercial unit. The catalysts were then subjected to a selective oxidation test similar in nature to that set forth in Example V above. Periodic examination and testing resulted in the figures set forth in Tables 3 and 4 below.

TABLE 3

| Oxygen Conversion of Aged Catalysts (%) | | | | |
|---|---|---|---|---|
| | CATALYST | | | |
| Hours on Stream | A | B | C | D |
| 3 | 69 | 74.5 | 76 | 81 |
| 12 | 74.5 | 72.5 | 68 | 77.5 |
| 18 | 73 | 71 | 65 | 81.5 |
| 24 | 72 | 71 | 62.5 | 78 |

TABLE 4

| Styrene Combustion Selectivity of Aged Catalysts (%) | | | | |
|---|---|---|---|---|
| | CATALYST | | | |
| Hours on Stream | A | B | C | D |
| 3 | 22.8 | 28.5 | 18 | 18 |
| 12 | 18.5 | 22.8 | 19 | 18.5 |
| 18 | 18 | 22 | 20 | 13.5 |
| 24 | 17.5 | 22.5 | 18 | 15.5 |

Again it is to be noted that the catalyst of the present invention which was prepared in a two-step impregnation process exhibited greater stability and activity than was exhibited by catalysts known in the art.

EXAMPLE VII

As another indication of the superiorty of the catalyst of the present invention, temperature profile measurements were performed during the course of the tests that showed that the catalyst of the present invention was a more active catalyst than those previously known. For more active catalysts, less heat is required to maintain a desired operating temperature of about 600° C.; lower inlet temperatures may be employed since bed exotherm is greater. This is evidenced by the following table showing the temperature differential ($T_{max} - T_{inlet}$) in which the greater $\Delta T$ indicates the more active catalyst.

TABLE 5

| | Temperature Differential | | | |
|---|---|---|---|---|
| CATALYST | A | B | C | D |
| $\Delta T$ Fresh | 38 | 45 | 50 | 51 |

TABLE 5-continued

| CATALYST | Temperature Differential | | | |
|---|---|---|---|---|
| | A | B | C | D |
| ΔT Aged | 23 | 33 | 26 | 35 |

I claim as my invention:

1. In a process for the dehydrogenation of a dehydrogentable hydrocarbon with separate and intermediate selective oxidation of hydrogen which comprises the steps of:
 (a) contacting said hydrocarbon with a dehydrogenation catalyst comprising an alkaline metal-promoted iron compound in a first reaction dehydrogenation zone in the presence of steam at dehydrogenation conditions to produce a first reaction dehydrogenation zone effluent stream comprising a mixture of dehydrogenated hydrocarbons, unconverted hydrocarbons, hydrogen and steam;
 (b) removing said first reaction dehydrogenation zone effluent stream from said first dehydrogenation zone;
 (c) passing said effluent stream of step (b) to a second reaction oxidation zone which is separate and discrete from said first reaction dehydrogenation zone;
 (d) contacting said first dehydrogenation zone effluent stream in said second reaction oxidation zone with oxygen-containing gas in the presence of an oxidation catalyst consisting essentially of a Group VIII noble metal, a Group IVA metal, and lithium composited on a solid porous support at oxidation conditions to selectively oxidize said hydrogen within said first reaction zone effluent stream to the substantial exclusion of oxidation of said dehydrogenated and unconverted hydrocarbons, wherein said selective oxidation of said hydrogen is exothermic in nature to provide additional heat and thereby raise the temperature of said dehydrogenated and unconverted hydrocarbons;
 (e) withdrawing a dehydrogenated and unconverted hydrocarbon effluent stream from said second reaction oxidation zone having an increased temperature with respect to the temperature of said first reaction dehydrogenation zone effluent stream;
 (f) passing said second reaction oxidation zone product effluent stream of step (e) at dehydrogenation conditions to a third reaction dehydrogenation zone containing a dehydrogenation catalyst comprising an alkaline metal-promoted iron compound to produce dehydrogenated hydrocarbons; and
 (g) withdrawing and recovering said dehydrogenated hydrocarbons, the improvement which comprises utilizing as said selective oxidation catalyst a composite which has been prepared by the steps of impregnating a solid porous support which a compound containing a Group VIII noble metal and a compound containing a Group IVA metal, calcining said impregnated support and sequentially impregnating said calcined impregnated support with a compound containing lithium.

2. The process as set forth in claim 1 in which said Group VIII noble metal is present in said oxidation catalyst in an amount in the range of from about 0.01% to about 5% by weight of said catalyst.

3. The process as set forth in claim 1 in which said Group IVA metal is present in said oxidation catalyst in an amount in the range of from about 0.005% to about 5% by weight of said catalyst.

4. The process as set forth in claim 1 in which said lithium is present in said oxidation catalyst in an amount in the range of from about 0.05% to about 5% by weight of said catalyst.

5. The process as set forth in claim 2 in which said Group VIII noble metal is selected from the group consisting of platinum, palladium and rhodium.

6. The process as set forth in claim 3 in which said Group IVA metal is selected from the group consisting of germanium, lead and tin.

7. The process as set forth in claim 1 in which said solid porous support comprises alumina.

8. The process as set forth in claim 1 in which said alkaline metal of said dehydrogenation catalyst is selected from the group consisting of Groups IA and IIA of the Periodic Table.

9. The process as set forth in claim 1 in which said dehydrogenation catalyst contains an oxide or sulfide of metal selected from the group consisting of Groups IVB, VB and VIB of the Periodic Table.

10. The process as set forth in claim 1 in which said dehydrogenation and oxidation conditions include a temperature in the range of from about 500° to about 700° C. and a pressure in the range of from about 0.1 to about 10 atmospheres.

11. The process as set forth in claim 1 in which said oxygen-containing gas is air.

12. The process as set forth in claim 1 in which said oxygen-containing gas is a mixture of oxygen and steam.

13. The process as set forth in claim 1 in which said dehydrogenatable hydrocarbon is ethylbenzene and said dehydrogenated hydrocarbon is styrene.

14. The process as set forth in claim 1 in which said dehydrogenatable hydrocarbon is p-diethylbenzene and said dehydrogenated hydrocarbon is p-divnylbenzene.

15. The process as set forth in claim 1 in which said dehydrogenatable hydrocarbon is o-diethylbenzene and said dehydrogenated hydrocarbon is o-divinylbenzene.

16. The process as set forth in claim 1 in which said dehydrogenatable hydrocarbon is m-diethylbenzene and said dehydrogenated hydrocarbon is m-divinylbenzene.

17. The process as set forth in claim 1 in which said dehydrogenatable hydrocarbon is p-ethyltoluene and said dehydrogenated hydrocarbon is p-methylstyrene.

* * * * *